United States Patent
Ciancarelli

(10) Patent No.: US 9,694,135 B2
(45) Date of Patent: Jul. 4, 2017

(54) REVOLVING MULTI-CARTRIDGE HYPODERMIC SYRINGE AND METHOD OF USE

(71) Applicant: Nicholas Ciancarelli, East Boston, MA (US)

(72) Inventor: Nicholas Ciancarelli, East Boston, MA (US)

(*) Notice: Subject to any disclaimer, the term of this patent is extended or adjusted under 35 U.S.C. 154(b) by 419 days.

(21) Appl. No.: 14/374,491

(22) PCT Filed: Feb. 12, 2013

(86) PCT No.: PCT/US2013/025757
§ 371 (c)(1),
(2) Date: Jul. 24, 2014

(87) PCT Pub. No.: WO2013/122943
PCT Pub. Date: Aug. 22, 2013

(65) Prior Publication Data
US 2014/0364831 A1 Dec. 11, 2014

Related U.S. Application Data

(60) Provisional application No. 61/598,661, filed on Feb. 14, 2012.

(51) Int. Cl.
*A61M 5/24* (2006.01)
*A61M 5/19* (2006.01)
(Continued)

(52) U.S. Cl.
CPC ............ *A61M 5/2448* (2013.01); *A61M 5/24* (2013.01); *A61M 5/19* (2013.01); *A61M 5/31515* (2013.01);
(Continued)

(58) Field of Classification Search
CPC .... A61M 5/24; A61M 5/2422; A61M 5/2429; A61M 2005/005; A61M 5/2414;
(Continued)

(56) References Cited

U.S. PATENT DOCUMENTS 842,631 A * 1/1907 Deperdussin ..... A61M 37/0069
604/62
1,109,072 A * 9/1914 Kozmousky ...... A61M 37/0069
604/62
(Continued)

FOREIGN PATENT DOCUMENTS

AT 410397 4/2003
GB 1525841 9/1978
(Continued)

OTHER PUBLICATIONS

International Search Report for International Application PCT/US2013/025757, dated May 30, 2013.
(Continued)

*Primary Examiner* — Kami A Bosworth
(74) *Attorney, Agent, or Firm* — Sean D. Detweiler, Esq.; Morse, Barnes-Brown & Pendleton, P.C.

(57) ABSTRACT

A revolving multi-cartridge syringe device includes a needle and two or three revolving holders, each for receiving a cartridge containing medical fluid to be injected. The holders can be pre-loaded with the cartridges, with a first cartridge placed in a loaded position ready to dispense. After fluid in the first cartridge is injected into a patient, a second holder and cartridge are revolved into the loaded position, without breakdown of the syringe. The process can be repeated with a third cartridge. The engagement of each cartridge with the needle, retraction from the needle, and rotation of the revolving holder are all implemented by sliding a sliding actuator in either a first direction or a second, opposite, direction, depending on which action is desired. Thus,
(Continued)

injection and reloading of the cartridges can be easily actuated by the user through manipulation of a single slidable actuator, without requiring withdrawing the needle from the mouth area to reload.

18 Claims, 11 Drawing Sheets

(51) Int. Cl.
  *A61M 5/315* (2006.01)
  *A61M 5/00* (2006.01)
(52) U.S. Cl.
  CPC ............... *A61M 2005/005* (2013.01); *A61M 2005/2407* (2013.01); *A61M 2005/247* (2013.01); *A61M 2005/2488* (2013.01); *A61M 2005/2496* (2013.01)
(58) Field of Classification Search
  CPC .. A61M 5/247; A61M 5/2481; A61M 5/2485; A61M 5/2488; A61M 5/2496; A61M 37/0069
  See application file for complete search history.

(56) References Cited

U.S. PATENT DOCUMENTS

| | | | | |
|---|---|---|---|---|
| 4,576,591 | A | * | 3/1986 | Kaye ................. A61M 37/0069 206/3 |
| 4,673,387 | A | * | 6/1987 | Phillips ............. A61M 37/0069 604/62 |
| 6,056,716 | A | | 5/2000 | D'Antonio et al. |
| 2011/0160674 | A1 | | 6/2011 | Holmes et al. |
| 2015/0011943 | A1 | | 1/2015 | Holmes et al. |

FOREIGN PATENT DOCUMENTS

| | | |
|---|---|---|
| WO | WO 98/17332 | 4/1998 |
| WO | WO 2009/113883 | 9/2009 |
| WO | WO 2010/048753 | 5/2010 |
| WO | WO 2011/143573 | 11/2011 |

OTHER PUBLICATIONS

Supplementary European Search Report for European Application No. EP13748859, dated Oct. 23, 2015.

* cited by examiner

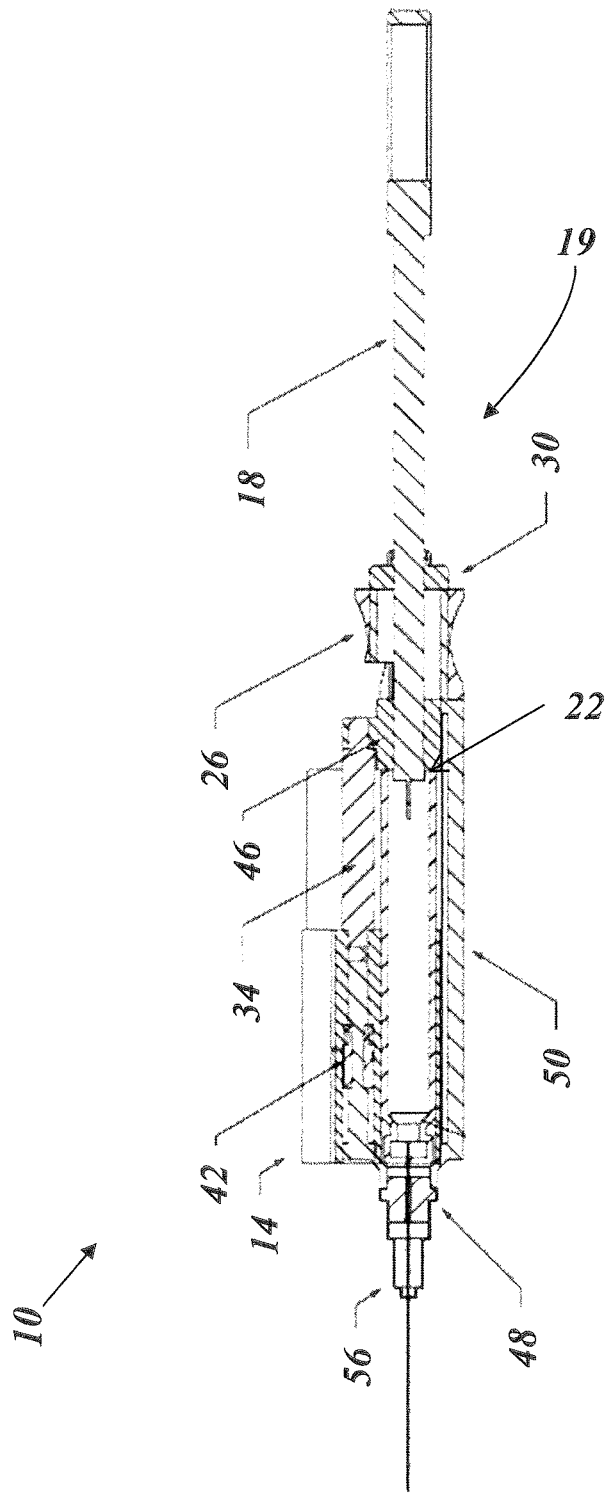
Fig. 5 (Along A-A)

REVOLVING MULTI-CARTRIDGE HYPODERMIC SYRINGE AND METHOD OF USE

RELATED APPLICATION

This application is a national stage filing under 35 U.S.C. 371 of International Application No. PCT/US2013/025757, filed Feb. 12, 2013, which claims priority to, and the benefit of, U.S. Provisional Application No. 61/598,661, filed Feb. 14, 2012, the teachings of which are hereby incorporated by reference in their entirety. International Application No. PCT/US2013/025757 was published under PCT Article 21 (2) in English.

FIELD OF THE INVENTION

The present invention relates to a hypodermic syringe for medical use, including dental, veterinarian, or other medical applications. More specifically, the present invention provides a syringe device designed to dispense multiple preloaded cartridges of anesthetic or medical fluid, one at a time, in consecutive order.

BACKGROUND

A more recent approach in dentistry is to treat patients by performing multiple required dental procedures during a single dental office visit. For example, in an approach commonly referred to as "quadrant dentistry," multiple (preferably all) dental conditions existing in a particular dental quadrant are treated together in a single, continuous procedure. This optimizes chair time for the dentist and minimizes patient visits. Combining multiple procedures together into a single visit (e.g., based on dental quadrant(s)) requires injection of multiple cartridges of anesthetic. Current self-aspirating syringes inject one cartridge of anesthetic per injection, using a plunger or harpoon style system that delivers the anesthetic to the area to be anesthetized. Thus, the current practice for dispensing several cartridges of anesthetic is to load a first cartridge into the syringe, inject the first cartridge, withdraw the syringe, remove the spent cartridges from the syringe, reload the syringe with a second cartridge, and inject the second cartridge. This procedure is repeated for all additional cartridges that are required to be injected for the particular operations being performed.

The above-described practice has several shortcomings. For example, the risk to of needle sticks to dental team members increases with the number of times the syringe must be removed and reloaded. Additionally, the fine gage needle used to inject the fluid into the tissue is more likely to become damaged during such reloading procedures. Furthermore, these reloading procedures (which require breakdown of the syringe) increase the amount of time required by such dental procedures. This additional time required to switch out cartridges can be distracting to the dentist, and can be expensive (e.g., in terms of opportunity costs). Furthermore, patients often feel greater discomfort during such reloading procedures, as the repeated lowering of a needle can be an intrusive and intimidating sight to bear.

U.S. Pat. No. 5,542,934 to Silver attempts to address some of the aforementioned problems by providing a syringe that is capable of simultaneously injecting two different cartridges to a patient. In particular, the syringe described in Silver includes two barrels laid side-by-side for receiving two cartridges. By manipulating a single finger ring, a plunger is depressed simultaneously against the two cartridges contained in the two barrels. Thus, the provision of two cartridges does somewhat increase the volume of fluid available for injection, but not to an amount sufficient for many present day procedures that can require three or more cartridges. In addition, the structure of the device of Silver includes a mixing chamber where the fluid exiting each cartridge must pool before traveling to the needle and exiting the device. Such mixing chambers can create difficulties in maintaining a sterile environment within the device.

SUMMARY

There is a need for a syringe device capable of multiple injections of medical fluid without requiring lengthy and cumbersome breakdown and reloading procedures, or repeated swapping out or removal of needle devices from the patient when working, for example, in a single quadrant area. The present invention is directed toward solutions to address this and other needs, in addition to having other desirable characteristics that will be appreciated by one of skill in the art upon reading the present specification.

In accordance with an embodiment of the present invention, a syringe device includes a needle. The syringe device also includes two or more holders each configured to receive a cartridge containing medical fluid to be injected. Also, the syringe device includes a body unit coupled to the needle and the two or more holders. The body unit is configured to receive one of the two or more holders in a loaded position at any one time. The syringe device also includes a slidable actuator slidably coupled to the body unit. The syringe device further includes a revolving unit coupled to the body unit and the two or more holders. The revolving unit is adapted to revolve the two or more holders one at a time into and out of the loaded position. The slidable actuator is configured in such a way as to engage the cartridge with the needle to effect fluid communication therebetween when the actuator slides in a first direction to an engagement position. The cartridge is disengaged from the needle when the actuator slides in a second direction opposite the first direction to a dis-engagement position. The actuator revolves the revolving unit when the actuator slides additionally in the second direction beyond the dis-engagement position to a revolve position.

In accordance with aspects of the present invention, the needle is a standard disposable needle secured to and through a hub.

In accordance with aspects of the present invention, the body unit further includes a guide member coupled to a backing piece for receiving one of the two or more holders in the loaded position. In a further aspect, a portion of the slidable actuator is situated in the guide member in such a way that the slidable actuator slides in the first direction and second direction relative to the guide member.

In accordance with aspects of the present invention, the revolving unit further includes a cog having a grooved track in an exterior surface of the cog. The grooved track of the cog engages a pin on the two or more holders to enable the revolving of the two or more holders as the pin travels along the grooved track. In a further aspect, the grooved track includes two or more curved peaks positioned at equal intervals around the cog.

In accordance with aspects of the present invention, the slidable actuator further includes an engagement member that engages the cartridge in one of the holders in the loaded position. In a further aspect, the engagement member is a latching member. In an alternative aspect, the engagement member is a pushing member.

In accordance with aspects of the present invention, the syringe device further includes a finger handle forming a portion of the actuator configured in such a way as to enable engagement of the actuator with a single finger or thumb of a user. In a further aspect, the finger handle is O-shaped.

In accordance with an embodiment of the present invention, a syringe device includes a needle. The syringe device also includes three or more holders each configured to receive a cartridge containing medical fluid to be injected. Also, the syringe device includes a body unit coupled to the needle and the three or more holders. The body unit is configured to receive one of the three or more holders in a loaded position at any one time. The syringe device also includes a slidable actuator slidably coupled to the body unit. The syringe device further includes a revolving unit coupled to the body unit and the three or more holders. The revolving unit is adapted to revolve the three or more holders one at a time into and out of the loaded position. The slidable actuator is configured in such a way as to engage the cartridge with the needle to effect fluid communication therebetween when the actuator slides in a first direction to an engagement position. The cartridge is disengaged from the needle when the actuator slides in a second direction opposite the first direction to a dis-engagement position. The actuator revolves the revolving unit when the actuator slides additionally in the second direction beyond the dis-engagement position to a revolve position.

In accordance with an embodiment of the present invention, a method of using a syringe device includes providing two or more cartridges containing medical fluid. Using a slidable actuator, one of the two or more cartridges is engaged in a loaded position with a needle to effect fluid communication between the needle and the cartridge in the loaded position. The medical fluid contained in the cartridge in the loaded position is injected, using the slidable actuator, into a targeted tissue location. Using the slidable actuator, the cartridge in the loaded position is disengaged from the needle. Using the slidable actuator, a revolving unit is revolved to cause the cartridge in the loaded position to be revolved out of the loaded position and to cause another cartridge of the two or more cartridges to be revolved into the loaded position.

In accordance with aspects of the present invention, the step of engaging the cartridge by the slidable actuator further includes sliding the slidable actuator in a direction toward the needle.

In accordance with aspects of the present invention, the cartridge being disengaged by the slidable actuator further includes sliding the slidable actuator in a direction away from the needle to a dis-engagement position. In a further aspect, revolving a revolving unit includes sliding the slidable actuator additionally in the direction away from the needle beyond the dis-engagement position to a revolve position.

In accordance with aspects of the present invention, the revolving unit further includes a cog having a grooved track in an exterior surface of the cog configured in such a way that the grooved track of the cog engages a pin on two or more holders which receive the two or more cartridges. This causes the revolving of the two or more cartridges as the pin travels along the grooved track. In a further aspect, the pin reaches a valley in the grooved track causing one of the two or more holders to revolve into the loaded position.

BRIEF DESCRIPTION OF THE FIGURES

These and other characteristics of the present invention will be more fully understood by reference to the following detailed description in conjunction with the attached drawings, in which:

FIG. 5 is a cross-sectional view of the syringe device along line A-A of FIG. 4, according to aspects of the present invention;

DETAILED DESCRIPTION

Figure 1:
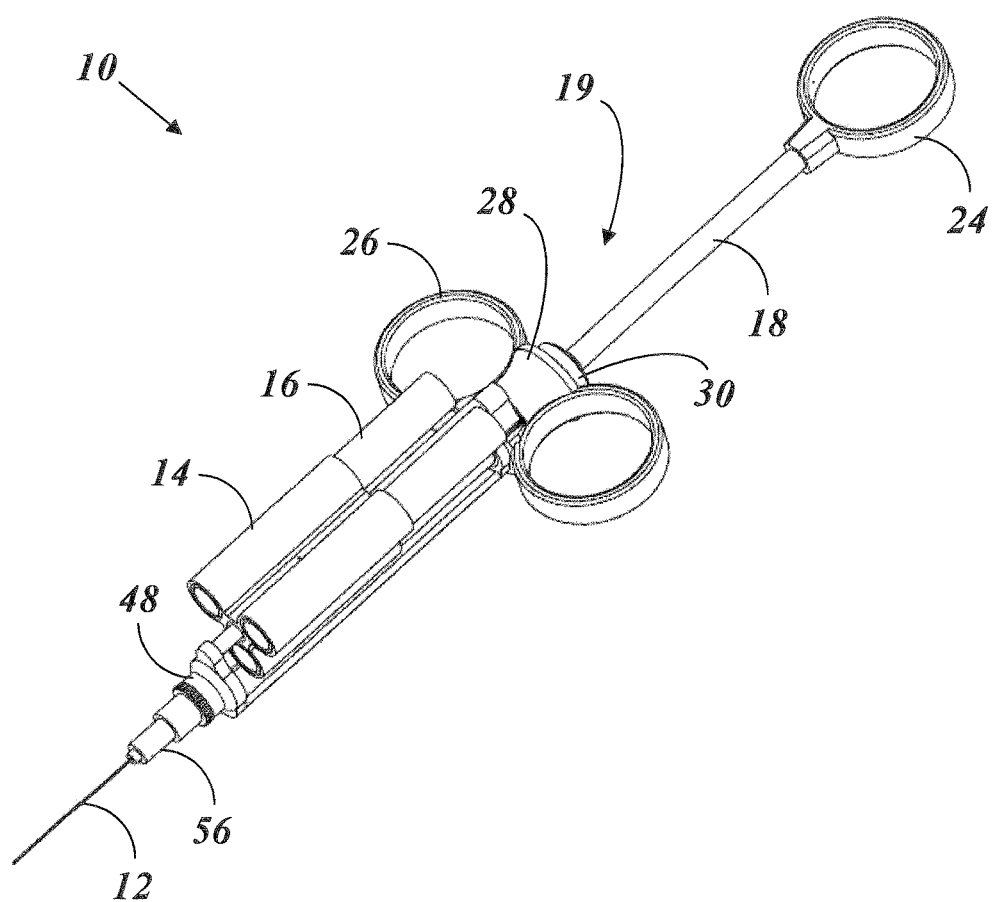
FIG. 1 is a perspective view of a syringe device, according to an example embodiment of the present invention.
Figure 2:
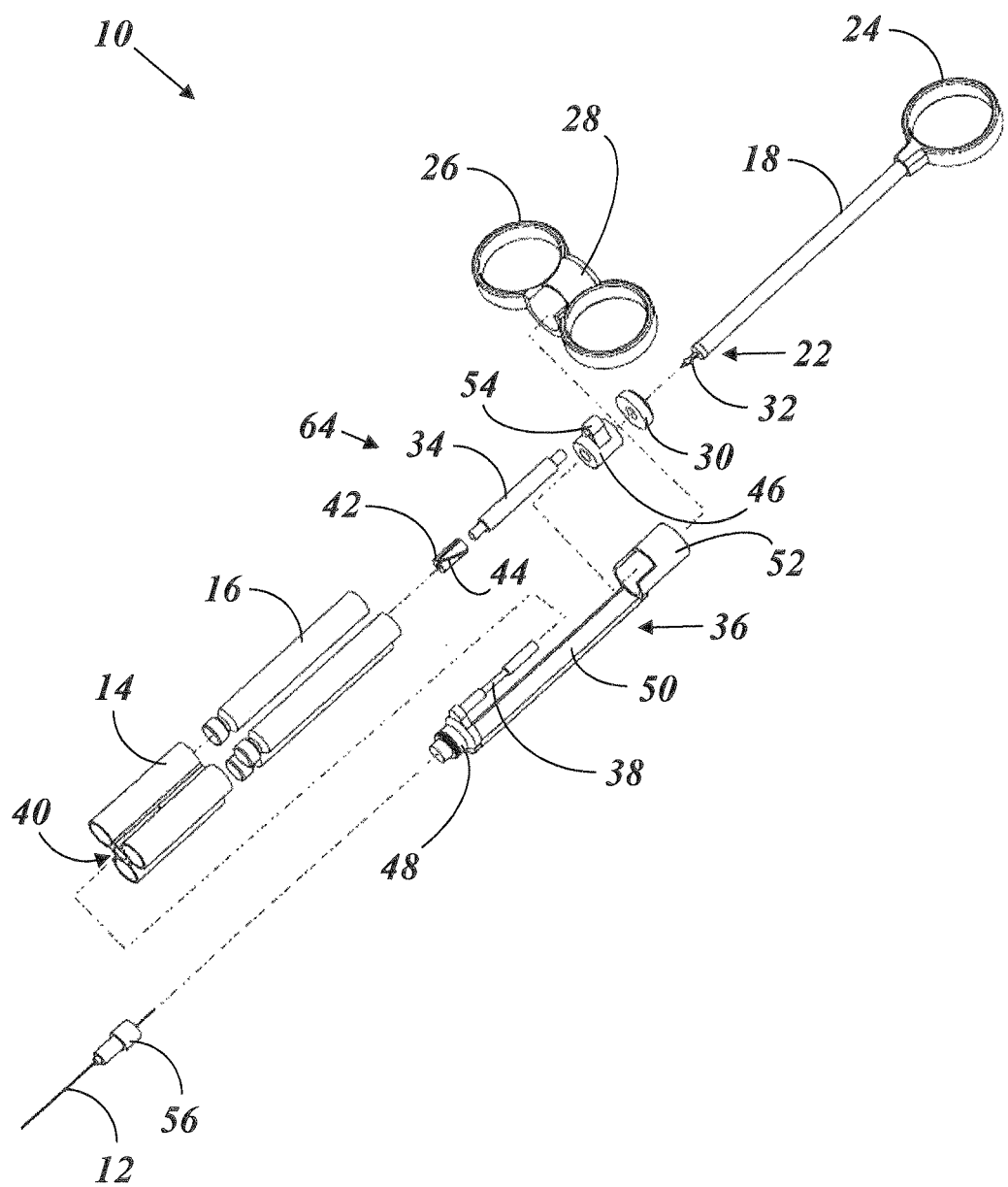
FIG. 2 is an exploded perspective view of the syringe device of FIG. 1, depicting various component parts, according to aspects of the present invention.

An illustrative embodiment of the present invention relates to a revolving multi-cartridge syringe device (e.g., a self-aspiring hypodermic syringe device). The syringe device includes a needle and three revolving holders each for receiving a cartridge containing medical fluid to be injected. The holders can all be pre-loaded with the cartridges, with a first cartridge immediately being placed in a loaded position ready to dispense prior to insertion of the needle into a targeted tissue location of a patient. After fluid in the first cartridge is injected, a second cartridge in a second holder is revolved into the loaded position, without breakdown of the syringe or reloading of additional cartridges. After the user injects fluid in the second cartridge contained in the second holder, the user can easily cause a third cartridge contained in a third holder to be revolved into the loaded position for subsequent injection into the patient. For each of the three cartridges, the fluid can be injected and aspired (as needed) by depressing (and optionally retracting) a slidable actuator. Furthermore, revolving motion of the cartridges can be actuated by pulling the actuator in an extended direction away from the needle once the actuator is in a fully retracted position. Thus, injection and reloading of the cartridges can be easily actuated by the user through manipulation of a single finger slidable actuator. Due to the feature of multiple cartridges being revolved into a loaded position, the needle does not need to be withdrawn from a patient's mouth area during a procedure to reload. Thus, repeated swapping out or removal of the needle device from the patient is no longer required.

FIGS. 1 through 9, wherein like parts are designated by like reference numerals throughout, illustrate example embodiments of a revolving multi-cartridge syringe device (e.g., a self-aspiring hypodermic syringe device), according to the present invention. Although the present invention will be described with reference to the example embodiments illustrated in the figures, it should be understood that many alternative forms can embody the present invention. One of skill in the art will additionally appreciate different ways to alter the parameters of the embodiments disclosed, such as the size, shape, or type of elements or materials, in a manner still in keeping with the spirit and scope of the present invention.

Referring now to FIGS. 1 through 5, a revolving multi-cartridge syringe device 10 (e.g., a self-aspiring hypodermic syringe device) is depicted according to an example embodiment of the present invention. The syringe device 10 includes a needle 12 situated at a front-most tip for delivery of medical fluid to a patient. The needle 12 can be a standard disposable needle that is secured to a pre-threaded hub 56 (e.g., made of plastic). The needle 12 passes through the hub 56 in such a way as to extend beyond both the forward and rearward ends of the hub 56. As would be appreciated by one of skill in the art, the needle 12 and the hub 56 can be conventional needle components, which are commonly sold together as a collective unit, e.g., by third-party suppliers or companies. The hub 56 secures to (e.g., screws onto) a base element 48 of the syringe device 10.

The syringe device 10 also includes three cylindrical holders 14 (e.g., barrel-shaped) adapted to revolve into and out of loaded and unloaded positions. The holders 14 have central axes that are substantially parallel to one another and are coupled together in such a way as to form a central channel 40. The holders 14 are situated at evenly distributed positions around the central channel 40, such that each holder 14 is substantially an equal distance apart from the other two holders 14. Each of the holders 14 is at least partially open on both ends. Each holder 14 is shaped and sized to receive and hold a cartridge 16 containing a fluid (e.g., anesthetic) to be injected by the syringe device 10. The cartridges 16 can be, for example, a fully sealed, rigid, cylindrical container capable of being pierced on its front end to allow the fluid contained therein to be released to the needle 12. In illustrative embodiments, each cartridge 16 includes a rubber end cap situated at a rearward end of the cartridge 16. For example, the rubber end cap forms a housing element that defines an inner chamber containing the fluid (e.g., anesthetic) to be injected. This example illustrates a carpule-type cartridge. One of skill in the art will appreciate that the syringe device 10 of the present invention can be sized and dimensioned for particular purposes. Specifically, should different cartridges 16 of different sizes, shapes, or dimensions be required, the present invention can be manufactured in different sizes, shapes, or dimensions, to accommodate such variations. In addition, it should be noted that the fluid contained within the cartridges 16 for delivery through the syringe device 10 can vary depending on the particular medical use (e.g., dental, veterinarian, surgical, or the like), and the therapeutic or medical effect or purpose of such fluid is not limiting to the present invention. Furthermore, although only three holders 14 are depicted in FIGS. 1 through 5, in other examples, more holders 14 are included, as would be appreciated by one of skill in the art upon reading the present specification. Alternatively, in another example, only two holders are used.

A body unit 36 is adapted to hold one of the cartridges 16 at a time in a loaded position and enable each of the cartridges 16 to be revolved into and out of a loaded and an unloaded position. The body unit 36 includes a fixed rod 38 coupled by the base element 48 to an elongate backing piece 50. The fixed rod 38 and the elongate backing piece 50 are oriented such that their central axes are substantially parallel.

The body unit 36 also includes a cylindrical guide member 52 coupled to the backing piece 50. A movable bearing 46 is situated in the guide member 52 in such a way that the bearing 46 is enabled to slide rearward and forward relative to the guide member 52 when the body unit 36 is in a loaded position. The fixed rod 38 and the backing piece 50 are positioned in such a way as to form a loaded space therebetween defining the loaded position. A cartridge 16 is loaded into the syringe device 10 by placing the cartridge 16 in an empty holder 14 and subsequently revolving the formerly-empty holder 14 into the loaded position defined by the space between the fixed rod 38 and the backing piece 50. The rearward portion of the needle 12 extends through the base element 48, such that the needle 12 is adapted to puncture the forward facing end of a loaded cartridge 16 to establish fluid communication between the needle 12 and the cartridge 16.

Revolving motion of the holders 14 into and out of the loaded position is enabled in part by a revolving unit 64. In the example embodiment of FIGS. 1 through 5, the revolving unit 64 includes a cog 42 with a grooved track 44 formed in an exterior surface thereof. The cog 42 is situated in the central channel 40 between the three holders 14 and engages the three holders 14 in a manner enabling rotation of the three holders 14 about the cog 42. In particular, a pin 66 extends from one or more walls forming the central channel 40 formed by the three holders 14. The pin 66 is slidably situated in the grooved track 44 of the cog 42, such that the grooved track 44 defines a restricted pathway along which the pin 66 on the holders 14 follows during revolving motion of the holders 14 about the cog 42. Stated differently, motion of the pin 66 is restricted to the pathway defined by the grooved track 44. Although only one pin 66 is depicted and described with reference to the example embodiment provided herein, one of skill in the art will appreciate that more pins 66 can be included.

The fixed rod 38 passes through the forward end of the central channel 40 and is situated in the central channel 40 in such a way that the holders 14 are enabled to rotate about the fixed rod 38. The cog 42 is mounted on the fixed rod 38 in the central channel 40 and is situated at a substantially fixed lengthwise position along the fixed rod 38. The lengths of the cog 42, the fixed rod 38, and the central channel 40 all lie on the same axis. Thus, in the example embodiment depicted in FIGS. 1 through 5—in which the cog 42, the fixed rod 38, and the central channel 40 are all cylindrically shaped—the cog 42, the fixed rod 38, and the central channel 40 are all coaxial. A first end of a dowel 34 extends into the rearward end of the central channel 40 and is coupled to the holders 14 thereat. A second end of the dowel 34 is coupled to a side of the bearing 46, thus establishing an additional point of connection between the revolving unit 64 to the body unit 36, e.g., for providing greater stability and durability of the syringe device 10. For example, as depicted in the example embodiments of FIGS. 1 through 5, the dowel 34 is coupled to a projection 54 extending outward (e.g., perpendicularly) from a side of the bearing 46. The dowel 34 is coupled to the holders 14 and the bearing 46 in such a way that the holders 14 and the bearing 46 are separated by a substantially constant distance (length) at all times, while also enabling the holders 14 to rotate relative to the bearing 46.

A cylindrical shaft 18 slidably passes through the bearing 46 and through a rearward annular collar 30. The shaft 18 is adapted to force medical fluid contained in a loaded cartridge 16 through the needle 12. At the front end of the shaft 18 is a shaft head 22. The shaft head 22 can include or form an appropriately shaped (e.g., arrow-shaped, harpoon-shaped, etc.) latching member 32 capable of latching onto (e.g., by piercing slightly) the rubber end cap of a cartridge 16 situated in a holder 14 in the loaded position. Alternatively or additionally, the shaft head 22 can form a flat pushing member that compresses the cartridge 16 when the shaft 18 is depressed (i.e., advanced toward the front of the syringe device 10). These components (e.g. shaft 18, shaft head 22, bearing 46, rearward annular collar) collectively form the slidable actuator 19. The slidable actuator 19 is enabled to engage a cartridge 16 with the needle 12, inject medical fluid from the cartridge 16, disengage the cartridge 16 from the needle 12, and revolve the revolving unit 64. Other variations of components to form the slidable actuator 19 may be apparent to one of skill in the art in order to accomplish the same result. As such, the present invention is by no means limited to the particular combination of mechanical components utilized to implement the slidable actuator.

In the example embodiment of FIGS. 1 through 5, the syringe device 10 is adapted to be easily gripped by a user. An O-shaped finger handle 24 is coupled to a rearward end of the shaft 18 for receiving a finger (e.g., a thumb) of the user. Two O-shaped finger supports 26 are additionally included for allowing the user to grip the syringe device 10, e.g., by sliding his or her fingers therethrough. The two finger supports 26 are coupled by a support piece 28 that defines an annular passageway therethrough. The guide member 52 is fixedly situated in the passageway of the support piece 28.

Figure 3:
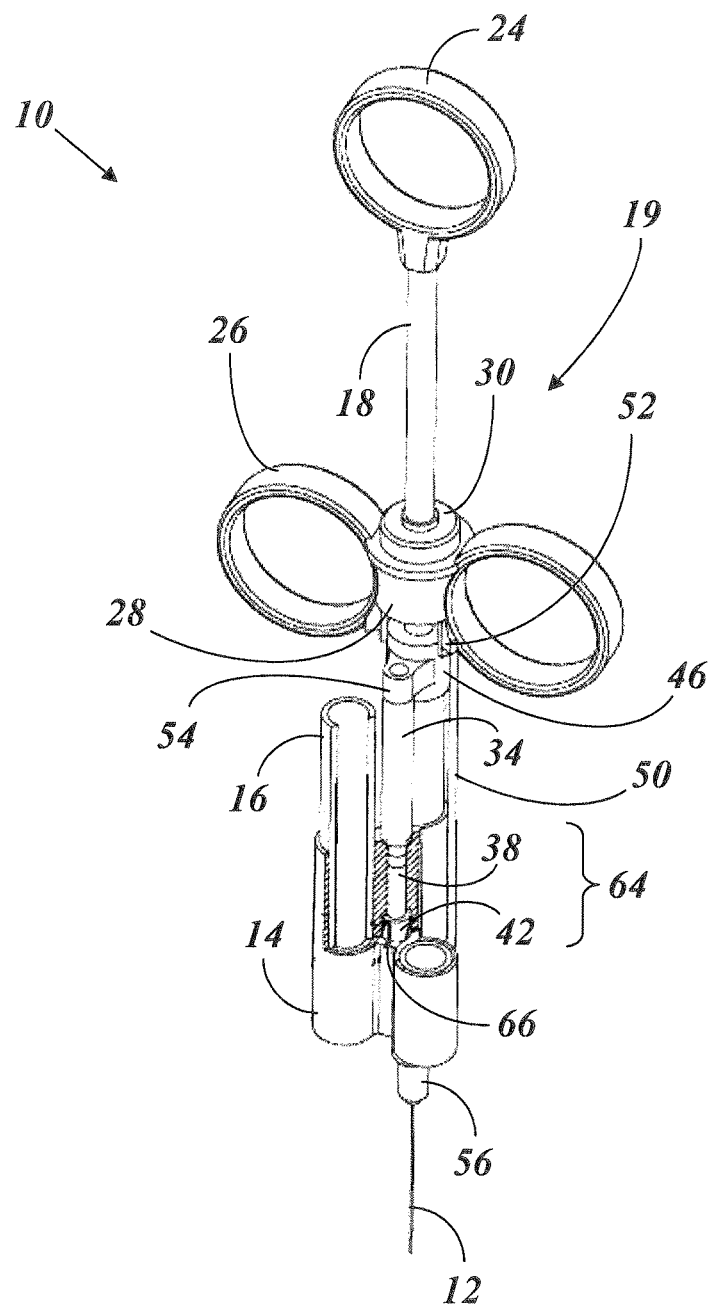
FIG. 3 is a partial cut-out view revealing various internal components of the syringe device of FIG. 1, according to one aspect of the present invention.
Figure 4:
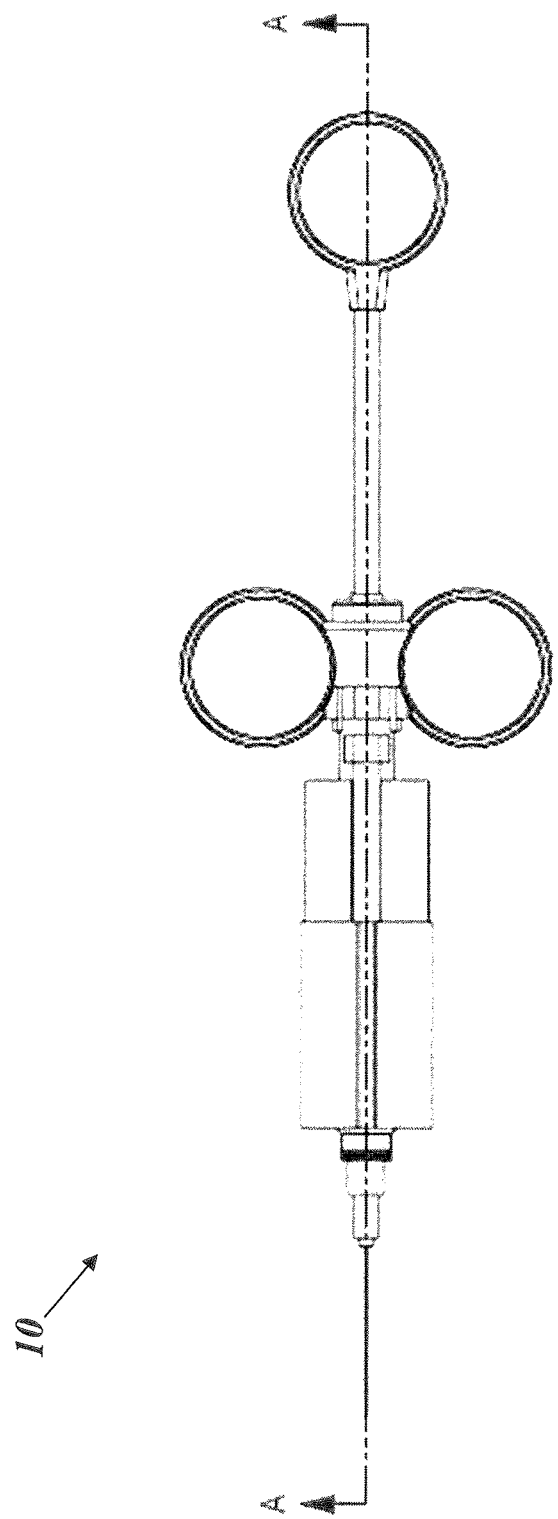
FIG. 4 is a side view of the syringe device of FIG. 1, according to aspects of the present invention.
Figure 6A:
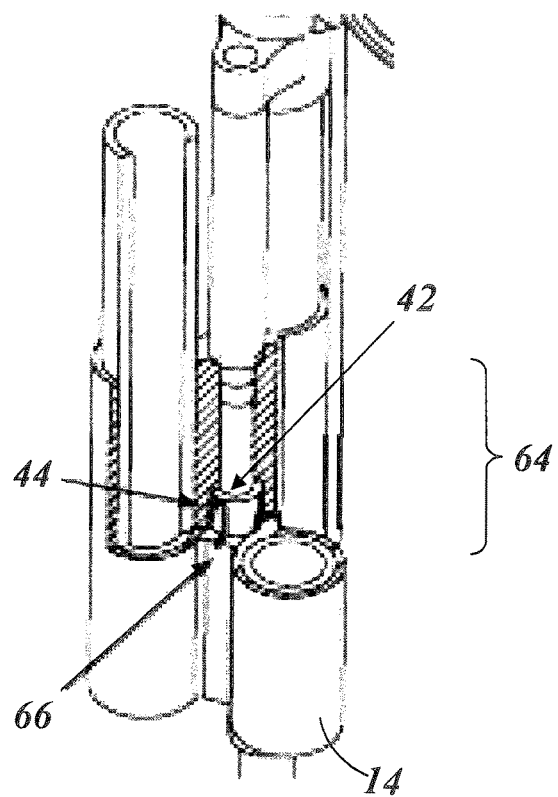
FIG. 6A is a close-up view of the partial cut-out view of FIG. 3 illustrating a cog in greater detail, according to aspects of the present invention.
Figure 6B:
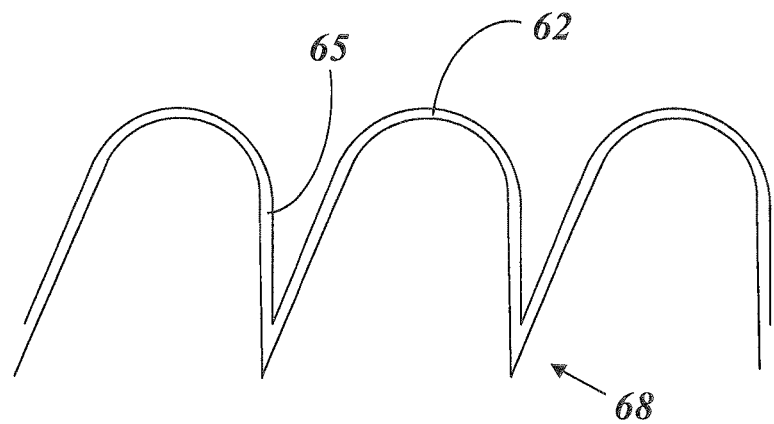
FIG. 6B is a flattened out view of a grooved track situated on an outer surface of the cog of FIG. 6A, according to aspects of the present invention.

Turning now to FIGS. 6A and 6B, the cog 42 and the grooved track 44 of the cog 42 is depicted in greater detail. FIG. 6A depicts a close-up view of the cog 42 as shown in FIG. 3. FIG. 6B depicts a flattened-out view of the grooved track 44 formed in the outer surface of the cog 42.

As illustrated in FIGS. 6A and 6B, the grooved track 44 defines a restricted pathway along which the pin 66 situated therein must travel during revolving motion of the holders 14. The grooved track 44 includes three smoothly curved peaks 62 on the outer surface of the cog 42 and positioned around the outer surface at about 120 degrees apart (for embodiments with three cylindrical holders 14). The three smoothly curved peaks 62 are connected by straight, vertical guides 65. The straight vertical guides 65 meet to form a valley 68 having a distorted V shape. Accordingly, during revolving motion around the cog 42, the pin 66 naturally stops at or falls into the valleys 68 (e.g., when the syringe device 10 is held upright as depicted in FIG. 3). Furthermore, the cog 42 is oriented relative to the body unit 36, and the pin 66 is oriented relative to the holders 14, in such a way that placement of the pin 66 in any of the valleys 68 causes one of the holders 14 to occupy the loaded position (i.e., the space between the fixed rod 38 and the backing piece 50). Thus, the grooved track 44 and the pin 66 are oriented in such a way that one of the holders 14 always naturally aligns in the loaded position for injection of the fluid.

Figure 7:
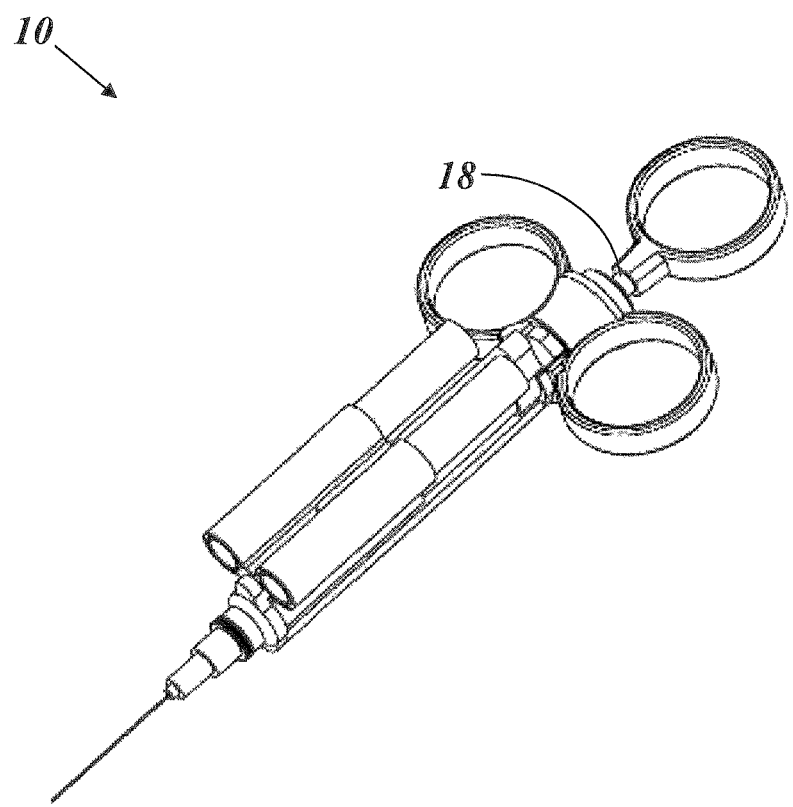
FIG. 7 is a perspective view of the syringe device of FIG. 1 with a plunger fully depressed during illustrative operation thereof.

In operation of the syringe device 10, fluid is injected from a loaded cartridge when the shaft 18 is depressed from a retracted position (i.e., advanced toward the front of the syringe device 10). Specifically, in embodiments where the shaft head 22 forms a latching member 32, the latching member 32 is advanced toward the loaded cartridge 16 until it engages or couples with (e.g., slightly pierces) the end cap of the loaded cartridge 16. As the shaft 18 is further depressed after engaging (coupling) with the end cap of the loaded cartridge 16, the shaft head 22 continues to apply pressure on the loaded cartridge 16, thereby causing the loaded cartridge 16 to press against the rearward portion of the needle 12 in an amount sufficient to puncture the forward end of the loaded cartridge 16. The shaft head 22 then can be slightly advanced and reversed to aspirate, if needed. The shaft head 22 subsequently can be smoothly depressed (advanced toward the front of the needle 12) to continually release the medical fluid from the loaded cartridge 16 to the needle 12, e.g., until the shaft 18 is fully depressed. For example, FIG. 7 depicts the syringe device 10 with the shaft 18 fully depressed. In this example, the syringe device 10 has two holders 14.

For embodiments in which the shaft head 22 forms a flat pushing member, the shaft 18 can be depressed smoothly, such that the shaft head 22 presses against the rearward end of the cartridge 16, thereby causing the back end of the needle 12 to puncture the front end of the cartridge 16 (e.g., the working end of the cartridge 16). Subsequent depression of the shaft 18 compresses the cartridge 16 and urges fluid through the needle 12. It should be noted that the specific type of shaft head 22, as well as its manner of operation, can be varied as would be appreciated by one of skill in the art to meet the needs of the particular intended medical application (e.g., veterinary medicine, dentistry, surgery, etc.). Embodiments of the present invention are not limited to the specific selections depicted in the figures and described herein, which are made for purposes of clarity and illustration.

Figure 8:
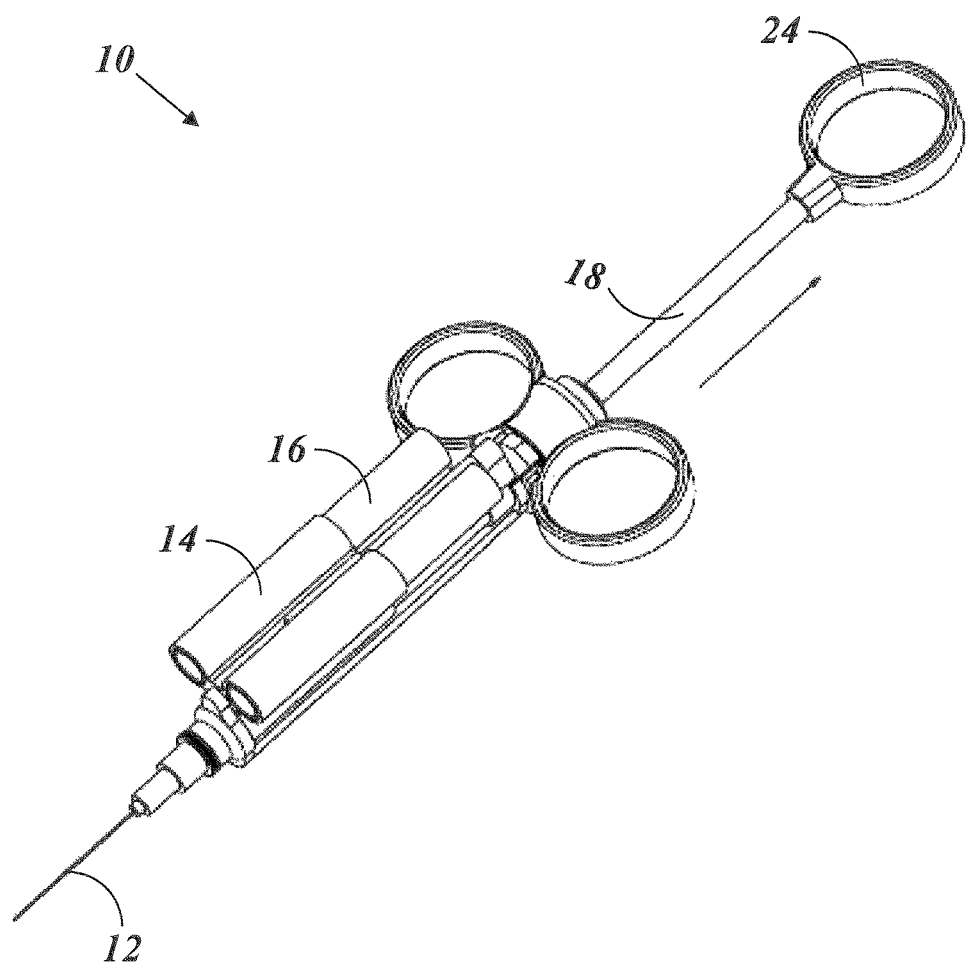
FIG. 8 is a perspective view of the syringe device of FIG. 7 with the plunger partially retracted during illustrative operation thereof.

Notably, after injecting medical fluid from a first cartridge 16 contained in a first holder 14, the syringe device 10 enables the user to easily revolve a remaining holder 14 containing an additional cartridge 16 into the loaded position, with minimal retraction of the needle 12 from the patient. For example, the user can retract the shaft 18 by pulling the finger handle 24 away from the needle 12, as depicted in FIG. 8. In this example, the syringe device 10 has two holders 14. As the shaft 18 is retracted, the latching member 32 remains at least initially coupled with the empty, used cartridge 16. Due to this coupling with the latching member 32, the empty, used cartridge 16 can be pulled in a direction away from the needle 12 as the shaft 18 is retracted (withdrawn) by the user, thereby disengaging the empty, used cartridge 16 from the needle 12. In illustrative embodiments, the holder 14 includes an inner lip or rim for catching the empty, used cartridge 16 and allowing the shaft 18 to be fully retracted from the holder 14 containing the empty, used cartridge 16. In one example, this inner lip or rim of each holder 14 has a specific shape designed for a specific cartridge (for example, based on type of cartridge or particular medicine used in the cartridge). This enables the holders 14 to only accept cartridges having a specific shape to fit the inner lip or rim of each holder 14 similar to a key having a specific shape for fitting within a lock or keyhole.

Figure 9:
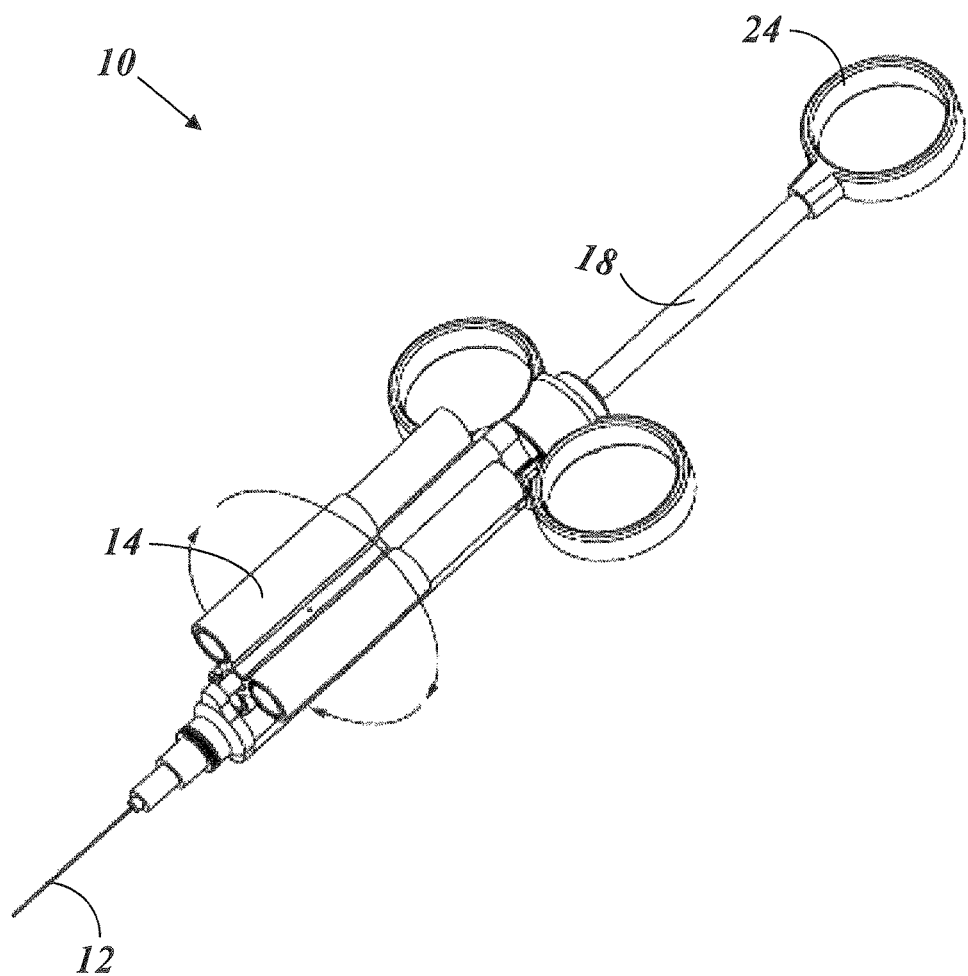
FIG. 9 is a perspective view of the syringe device of FIG. 8 with the plunger fully retracted during illustrative operation thereof.
Figure 10:
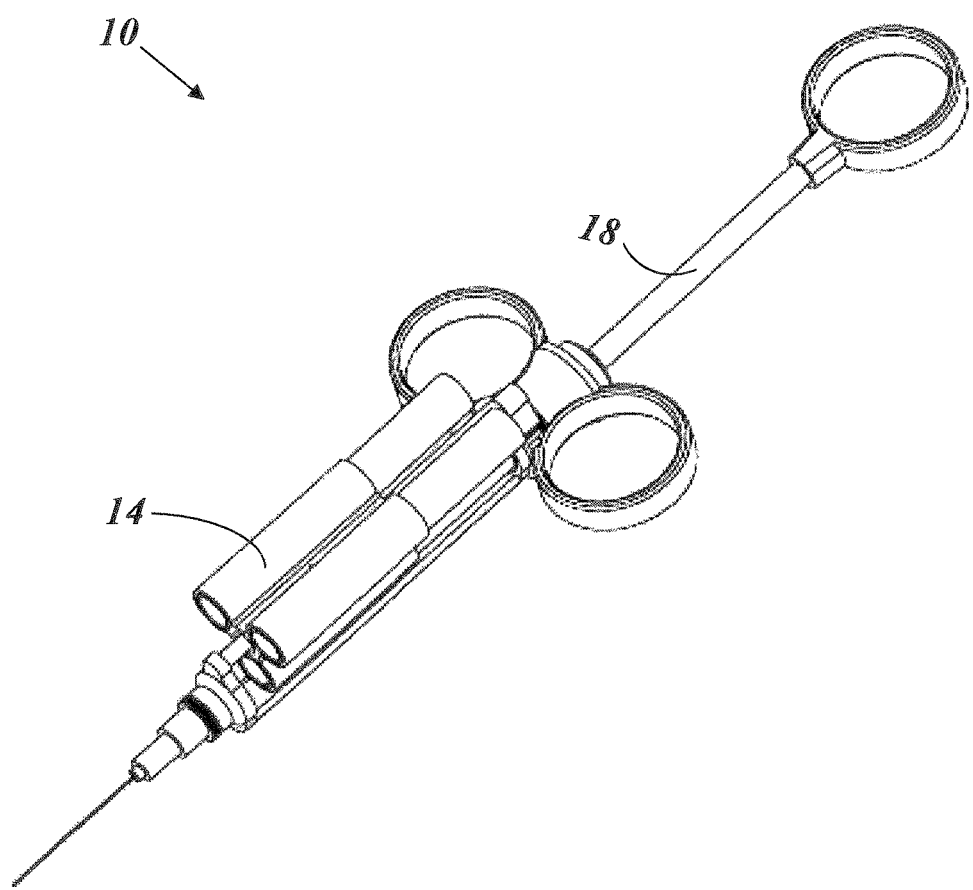
FIG. 10 is a perspective view of the syringe device of FIG. 9 with an unused cartridge having been revolved into a loaded position during illustrative operation thereof.

Once the shaft 18 is fully retracted from the holder 14, the user may actuate the revolving motion of the holders 14 around the cog 42 by further retracting the shaft 18 (e.g., by extending the finger handle 24 further outward and away from the needle 12), as depicted in FIG. 9. In this example, the syringe device 10 has two holders 14. In particular, additional retracting motion by the shaft 18 causes the shaft head 22 to press against the bearing 46 in a direction away from the needle 12. This causes the bearing 46 to slide in a direction away from the needle 12. As the bearing 46 slides away from the needle 12, so too does the dowel 34. Given that the dowel 34 is coupled at fixed lengthwise positions to both the bearing 46 and the holders 14, this sliding motion by the dowel 34 similarly causes the holders 14 to move in the same direction away from the needle 12. As the holders 14 are pulled by the dowel 34 in this manner, the pin 66 travels along the pathway defined by the grooved track 44, thereby causing the holders 14 to revolve around the cog 42. During the revolving motion, the holders 14 reach a maximum displacement from the base element 48 as the pin 66 reaches an adjacent curved peak 62 in the grooved track 44. This moment is depicted in FIG. 10. Further motion of the pin 66 along the grooved track 44 causes the holders 14 to continue to revolve until the pin 66 reaches an adjacent valley 68 along the grooved track 44. At this stage, a new holder 14 containing an unused cartridge 16 now occupies the loaded position. The shaft 18 then can be depressed to inject addition medical fluid contained in the unused cartridge 16, as described previously herein.

Figure 11:
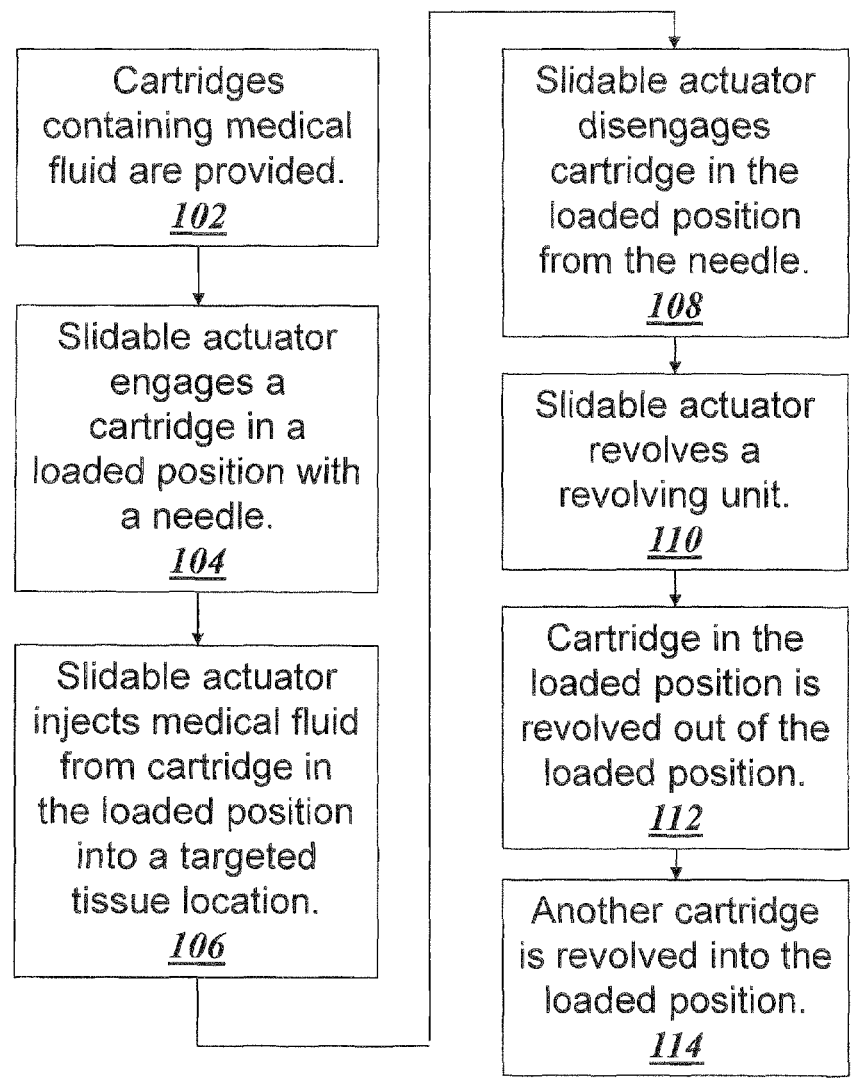
FIG. 11 is a flow chart diagram illustrating a method of using the syringe device, according to an example embodiment of the present invention.

FIG. 11 depicts a method of using the syringe device 10 according to an example embodiment of the present invention. In this example, cartridges 16 containing medical fluid are provided (step 102). A slidable actuator 19 is used to engage one of the cartridges 16 in a loaded position with a needle 12 (step 104) by moving the slidable actuator 19 in a first direction (toward the needle 12). This engagement causes fluid communication between the needle 12 and the cartridge 16 in the loaded position (i.e. by puncturing the cartridge, or otherwise accessing the inner chamber of the cartridge). Continuing to slide the slidable actuator 19 in the first direction transfers medical fluid from the cartridge 16 in the loaded position through the needle 12 and into a targeted tissue location (step 106) (within which the needle 12 has been located by the user). Sliding the slidable actuator 19 in a second direction opposite the first direction disengages the cartridge 16 in the loaded position from the needle 12 (step 108). With a continued sliding motion in the same, second, direction, the slidable actuator 19 revolves a revolving unit 64 (step 110). The revolving motion causes the cartridge 16 in the loaded position to be revolved out of the loaded position (step 112). Step 110 also causes another cartridge 16 to be revolved into the loaded position (step 114), such that the continued sliding movement of the slidable actuator 19 in the second direction causes execution of steps 108 through 114 (halt fluid flow, disengage the cartridge from the needle, revolve the spent cartridge out of the loaded position, and revolve a new cartridge into the loaded position). The method can then be repeated by sliding the actuator in the first direction again to engage the new cartridge.

In a further example, the slidable actuator 19 slides in a direction toward the needle 12 to cause the slidable actuator 19 to engage a cartridge 16 in the loaded position. Also, in a further example, the slidable actuator 19 slides in a direction away from the needle 12 to a dis-engagement position to cause the disengagement of the cartridge 16 in the loaded position from the needle 12. In a further example, the slidable actuator 19 slides additionally in the direction away from the needle 12 beyond the dis-engagement position to a revolve position causing the revolving of the revolving unit 64.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A syringe device, comprising:
a needle;
two or more holders each configured to receive a cartridge containing medical fluid to be injected;
a body unit coupled to the needle and the two or more holders and configured to receive one of the two or more holders and the cartridge of the one of the two or more holders in a loaded position at any one time;
a slidable actuator slidably coupled to the body unit; and
a revolving unit coupled to the body unit and the two or more holders, the revolving unit adapted to revolve the two or more holders one at a time into and out of the loaded position;
wherein the slidable actuator is configured in such a way as to engage the cartridge that is in the loaded position with the needle to effect fluid communication therebetween when the actuator slides in a first direction to an engagement position, disengage the cartridge that is in the loaded position from the needle when the actuator slides in a second direction opposite the first direction to a dis-engagement position, and revolve the revolving unit when the actuator slides additionally in the second direction beyond the dis-engagement position to a revolve position.

2. The syringe device of claim 1, wherein the needle is a disposable needle secured to and through a hub.

3. The syringe device of claim 1, wherein the body unit further comprises a guide member coupled to a backing piece for receiving one of the two or more holders in the loaded position.

4. The syringe device of claim 3, wherein a portion of the slidable actuator is situated in the guide member in such a way that the slidable actuator slides in the first direction and second direction relative to the guide member.

5. The syringe device of claim 1, wherein the revolving unit further comprises a cog having a grooved track in an exterior surface of the cog, the grooved track of the cog engages a pin on the two or more holders to enable the revolving of the two or more holders as the pin travels along the grooved track.

6. The syringe device of claim 5, wherein the grooved track comprises two or more curved peaks positioned at equal intervals around the cog.

7. The syringe device of claim 1, wherein the slidable actuator further comprises an engagement member that engages the cartridge that is in the loaded position.

8. The syringe device of claim 7, wherein the engagement member is a latching member.

9. The syringe device of claim 7, wherein the engagement member is a pushing member.

10. The syringe device of claim 1, further comprising a finger handle forming a portion of the actuator configured in such a way as to enable engagement of the actuator with a single finger or thumb of a user.

11. The syringe device of claim 10, wherein the finger handle is O-shaped.

12. A syringe device, comprising:
a needle;
three or more holders each configured to receive a cartridge containing medical fluid to be injected;
a body unit coupled to the needle and the three or more holders and configured to receive one of the three or more holders and the cartridge of the one of the three or more holders in a loaded position at any one time;
a slidable actuator slidably coupled to the body unit; and
a revolving unit coupled to the body unit and the three or more holders, the revolving unit adapted to revolve the three or more holders one at a time into and out of the loaded position;
wherein the slidable actuator is configured in such a way as to engage the cartridge that is in the loaded position with the needle to effect fluid communication therebetween when the actuator slides in a first direction to an engagement position, disengage the cartridge that is in the loaded position from the needle when the actuator slides in a second direction opposite the first direction to a dis-engagement position, and revolve the revolving unit when the actuator slides additionally in the second direction beyond the dis-engagement position to a revolve position.

13. A method of using a syringe device, comprising:
providing two or more cartridges containing medical fluid;
engaging, using a slidable actuator, one of the two or more cartridges in a loaded position with a needle to effect fluid communication between the needle and the cartridge of the one of the two or more cartridges in the loaded position;
injecting, using the slidable actuator, the medical fluid contained in the cartridge of the one of the two or more cartridges in the loaded position, into a targeted tissue location;
disengaging, using the slidable actuator, the cartridge of the one of the two or more cartridges in the loaded position from the needle; and
revolving, using the slidable actuator, a revolving unit to cause the cartridge of the one of the two or more cartridges in the loaded position to be revolved out of the loaded position and to cause another cartridge of the two or more cartridges to be revolved into the loaded position.

14. The method of claim 13, wherein the step of engaging further comprises sliding the slidable actuator in a direction toward the needle.

15. The method of claim 13, wherein the step of disengaging further comprises sliding the slidable actuator in a direction away from the needle to a dis-engagement position.

16. The method of claim 15, wherein revolving further comprises sliding the slidable actuator additionally in the direction away from the needle beyond the dis-engagement position to a revolve position.

17. The method of claim 13, wherein the revolving unit further comprises a cog having a grooved track in an exterior surface of the cog configured in such a way that the grooved track of the cog engages a pin on two or more holders, the two or more holders receiving the two or more cartridges, to cause the revolving of the two or more cartridges as the pin travels along the grooved track.

18. The method of claim 17, wherein the pin reaches a valley in the grooved track causing one of the two or more holders to revolve into the loaded position.

* * * * *